US008110204B2

(12) United States Patent
Khamar et al.

(10) Patent No.: US 8,110,204 B2
(45) Date of Patent: Feb. 7, 2012

(54) METHOD OF TREATING HUMAN-IMMUNODEFICIENCY VIRUS (HIV) DISEASE INFECTION

(75) Inventors: Bakulesh Mafatlal Khamar, Ahmedabad (IN); Indravadan Ambalal Modi, Ahmedabad (IN)

(73) Assignee: Cadila Pharmaceuticals Ltd., Ahmedabad, Gujarat (IN)

( * ) Notice: Subject to any disclaimer, the term of this patent is extended or adjusted under 35 U.S.C. 154(b) by 1204 days.

(21) Appl. No.: 10/468,467

(22) PCT Filed: Jan. 17, 2002

(86) PCT No.: PCT/IB02/00097
§ 371 (c)(1),
(2), (4) Date: Jan. 20, 2006

(87) PCT Pub. No.: WO02/056906
PCT Pub. Date: Jul. 25, 2002

(65) Prior Publication Data

US 2006/0193875 A1 Aug. 31, 2006

(30) Foreign Application Priority Data

Jan. 17, 2001 (IN) ............................... 49MUM2001

(51) Int. Cl.
*A61K 45/00* (2006.01)
*A01N 63/02* (2006.01)

(52) U.S. Cl. .................................... 424/282.1; 424/93.4

(58) Field of Classification Search ........................ None
See application file for complete search history.

(56) References Cited

OTHER PUBLICATIONS

Singh et al., In Vitro Characterization of T Cells from Mycobacterium w-Vaccinated Mice, Infection and Immunity, 1992, 60(1):257-263.*
Mehta et al., Impact of HIV Infection on Mycobacterial Disease, American Family Physician, 1992, 45(5):2203-2211.*
Yadava et al., T-cell Responses to Fractionated Antigens of Mycobacteriurn w, a Candidate Anti-Leprosy Vaccine, in Leprosy Patients, Scan. J. Immunol., 1991, 34:23-31.*
Post et al., Q J Med, 1996, 89:505-508.*
Mindel et al., BMJ, 2001, 322:1290-1293.*
Submits Angel et al., The Journal of Infectious Diseases, 1998, 177:898-904.*
Moss et al., Journal of Biomedical Science, 1997, 4:127-131.*

* cited by examiner

*Primary Examiner* — Zachariah Lucas
*Assistant Examiner* — Nicole Kinsey White
(74) *Attorney, Agent, or Firm* — Burns & Levinson LLP

(57) ABSTRACT

Human Immunodeficiency virus causes depletion of $CD_4$ cells. The depletion of $CD_4$ cells results in decrease in immunity of an infected individual. Due to decrease immunity various opportunistic infections occur. These infections are cause for morbidity and mortality in HIV infected individuals. The treatment of HIV these includes antiretroviral drugs. These drugs have their own side effects and immune reconstitution achieved is delayed and slow. Various attempts have been made to improve $CD_4$ count, use of IL-2 is one of them. It is associated with systemic side effects during the period of its administration. The present invention provides method of using *mycobacterium w* for the management of HIV. According to present invention *mycobacterium w* when given intradermally is effective in prophylaxis and treatment of AIDS or AIDS related complex (ARC). It is found to improve immunity as well as $CD_4$ count. It is found to eliminate symptoms like fever, diarrhea. The effect is seen even when no antiretrovirals are used.

29 Claims, 7 Drawing Sheets

Fig 1. HPLC analysis of crude extract obtained after disruption of Mycobacterium w cell by sonication.

Fig.2 HPLC analysis of methanol extract of Mycobacterium w.

Fig.3 HPLC analysis of chloroform extract of Mycobacterium w.

Fig.4 HPLC analysis of acetone extract of Mycobacterium w.

Regression analysis of Pre & Post treatment change in CD4 count when immunomodulator is being used alone Regression analysis of Pre & Post treatment change in CD4 count when immunomodulator is being used along with two antiretroviral drugs Regression analysis of Pre & Post treatment change in CD4 count when immunomodulator is being used along HAART therapy

METHOD OF TREATING HUMAN-IMMUNODEFICIENCY VIRUS (HIV) DISEASE INFECTION

This invention relates to the management of Human Immunodeficiency virus (HIV) Disease/Infection.

BACKGROUND OF THE INVENTION

Human immunodeficiency virus (HIV) was first isolated in 1983. The causative agent for AIDS is known to be a virus of the retrovirus family called HIV (human immunodeficiency virus). Infection with HIV does not, however, immediately give rise to overt symptoms of AIDS. Three to six weeks following primary HIV infection more than 50% of individuals develop acute HIV syndrome, which is self limiting. Clinical findings seen during this period include fever, pharyngitis, lymphadenopathy, headache, arthralgia, myalgia, malaise, lethargy, nausea, vomiting, diarrhea, skin rash, mucocutaneous ulceration, meningitis, encephalitis, neuropathy etc. The only indication of exposure to the virus may be the presence of antibodies thereto in the blood of an infected subject who is then described as 'HIV positive'. The infection may lie dormant; giving rise to no obvious symptoms, and the incubation period prior to development of AIDS may vary from several months to decades. Development of AIDS itself may be preceded by the AIDS-related complex (ARC), which is characterized by unexplained fever, weight loss, chronic cough or diarrhea. The development of AIDS and/or ARC is dependent on breakdown of immune system. The reasons for the variable period between infection with the virus and breakdown of the immune system in an infected individual are poorly understood. Factors at present unknown may trigger proliferation of the virus with consequential disruption of the immune system. The victims of the disease are then subject to various infections and malignancies, which, unchecked by the disabled immune system, lead to death. Thus HIV is characterized by the "acute HIV syndrome" followed by "asymptomatic stage" with clinical latency. Symptomatic stage sets in later with breakdown of immune system, which ultimately leads to the death of the individual infected with HIV.

Though the disease is caused by virus, the morbidity and mortality associated with disease is due to breakdown of immune system. The breakdown of immune system is characterized by decreased CD4+ T lymphocyte count. Because of this reason 1993 revised classification system for HIV infection is based on CD4+ T lymphocyte counts. HIV disease is empirically divided based on CD4+ count which is a measure of immunodeficiency.

a) Early stage CD4+ T cell count more than 500
b) Intermediate stage CD4+ T cell count 200 to 500.
c) Advanced stage CD4+ T cell count less than 200.

Individuals with nonprogressive HIV disease are found to have steady CD4+ counts. They are also observed to have strong immune response against the virus.

There is evidence that in HIV infection, there is a dramatic loss of CD4+ T-cells, which results in very rapid development of overt symptoms of AIDS. Most AIDs defining opportunistic infections and true malignancies occur in advanced stage of disease where in CD4+ count is less the 200 cells/μL.

CD4+ Count and HIV

Though HIV is a viral infection, viral load can be determined by reasonable accuracy, CD4+ count (a measure of immune status) plays major role in management of HIV due to following reasons.

1. Morbidity and Mortality in HIV infected individuals is due to opportunistic infections. These opportunistic infections define onset of AIDS in HIV +ve individuals. The risk of opportunistic disease increases markedly when CD4+ cell count declines to less than 200 cells/$mm^3$.
2. CD4+ count provides estimate of degree of existing immunodeficiency.
   Immune deficiency is responsible for HIV +ve individuals getting converted to AIDS.
3. The initiation of antiretroviral therapy is also dependent on CD4+ count.
4. Outcome of antiretroviral therapy is also dependent on CD4+ count. Higher survival are associated with higher initial CD4+ count.
5. Risk of progression to AIDs defining illness is associated with declining CD4+ count. The risk is lower with higher CD4+ count.
6. Likelyhood of developing AIDs within 3 years is significantly higher when CD4+ count is low (less than 200 CD4+ T cells) compared to high CD4+ T cell count. For viral load of greater than 55 k as per RT-PCR the risk is 32.6% if CD4+ T cell count is more than 500 cells/$mm^3$ compared to 85.5% for individuals with CD4+ count of less than 200 cells/$mm^3$.
7. Similarly for viral load of 20 k-55 k (RT-PCR) the risk of developing AIDs is 9.5% when CD4+ count is more than 750 cells/mm3 compared to 40.1% when CD4+ count is less than 350 cells/mm3.

Goals of Therapy

Maximal and durable suppression of viral load.
Restoration and/or preservation of immunologic function.
Improvement of quality of life.
Reduction in HIV related morbidity and mortality.

The method to treat HIV includes various therapeutic options. The options include management of symptoms and infections manifesting in HIV infected individuals at various stages of the disease. The antiretroviral drugs are used to keep the HIV infection (viral load) in control. They keep the viral load in control. The early antiretroviral drugs like azothymidine delayed progression of disease and had no significant effect on CD4+ count. Protease inhibitors like indinavir, ritonavir which are introduced recently do improve CD4+ count while reducing viral, load. All the drugs (antiretroviral) have their own side effects. The resistance to drugs is also noted. Thus there is need to provide alternate mechanism of treating HIV.

Since CD4+ count is important in maintaining immunity of individual and decreased CD4+ counts are associated with morbidity and mortality in HIV infection attempts are made to improve immunity for management of HIV. Various efforts have been done towards this end. This has resulted in introduction of immune modifying therapies with or without antiretroviral drugs. They comprise of antigens, cytokines organisms etc.

It has surprisingly been found during the course of research by us that formulations of '*Mycobacterium w*' (Mw) with or without antigenic and/or immunomodulatory material derived from (Mw) is effective for management of Human Immunodeficiency Virus (HIV) disease/infection.

PRIOR ART

*M. vaccae* is apparently unique among known mycobacterial species in that heat-killed preparations retain its properties for the use as vaccine and immunotherapeutic. For example, *M. bovis*-BCG vaccines, used for vaccination against tuberculosis, employ live strains. Heat-killed *M. bovis*

BCG and *M. tuberculosis* have no protective properties when employed in vaccines. A number of compounds have been isolated from a range of mycobacterial species, which have adjuvant properties. The effect of such adjuvants is essentially to stimulate a particular immune response mechanism against an antigen from another species.

In U.S. Pat. No. 6,001,361 the invention is related to compounds and methods for the treatment of mycobacterial infections including *Mycobacterium tuberculosis* and *Mycobacterium avium*. The invention is further related to compounds that function as non-specific immune response amplifiers, and the use of such non-specific immune response amplifiers as adjuvants in vaccination or immunotherapy against infectious disease, and in certain treatments for immune disorders and cancer.

U.S. Pat. No. 4,716,038 discloses diagnosis of, vaccination against and treatment of autoimmune diseases of various types, including arthritic diseases, by administering mycobacteria, including *M. vaccae*.

U.S. Pat. No. 6,210,684 describes method for delaying the onset of AIDS using killed *M. Vaccae*. Onset of AIDS is related to decrease in CD4+ count is not disclosed in the patent. Published studies shows that killed *M. Vaccae* has no effect on CD4+ count in HIV positive individuals.

International Patent Publication WO 91/01751 discloses the use of antigenic and/or immunoregulatory material from *M. vaccae* as an immunoprophylactic to delay and/or prevent the onset of AIDS.

International Patent Publication WO 94/06466 discloses the use of antigenic and/or immunoregulatory material derived from *M. vaccae* for therapy of HIV infection, with or without AIDS and with or without associated tuberculosis.

U.S. Pat. No. 6,001,361 discloses an invention that relates generally to the treatment by vaccination or immunotherapy of skin disorders such as psoriasis, atopic dermatis, allergic contact dermatitis, alopecia areata, and the skin cancers basal cell carcinoma, squamous cell carcinoma and melanoma. In particular, the invention is related to the use of compounds, which are present in or have been derived from *Mycobacterium vaccae* (*M. vaccae*) or from the culture filtrate of *M. vaccae*.

U.S. Pat. No. 5,599,545 discloses the use of mycobacteria, especially whole, inactivated *M. vaccae*, as an adjuvant for administration with antigens, which are not endogenous to *M. vaccae*. This publication theories that the beneficial effect as an adjuvant may be due to heat shock protein 65 (hsp 65).

International Patent Publication WO 92/08484 discloses the use of antigenic and/or immunoregulatory material derived from *M. vaccae* for the treatment of uveitis.

International Patent Publication WO 93/16727 discloses the use of antigenic and/or immunoregulatory material derived from *M. vaccae* for the treatment of mental diseases associated with an autoimmune reaction initiated by an infection.

International Patent Publication WO 95/26742 discloses the use of antigenic and/or immunoregulatory material derived from *M. vaccae* for delaying or preventing the growth or spread of tumors.

Vacce is not associated with change in CD4+ count or viral load in HIV positive individuals. It does not provide any relief in HIV +ve individual.

However inspite of various patents issued in relation to *mycobacterium vaccae*, it fails to provide any significant change in CD4+ count as well as viral load in individuals who are HIV positive.

Similarly attempts have been made to improve CD4+ count using immunomodulator from various sources.

Remune is a HIV-1 specific immunogen in incomplete Freund's adjuvant. It includes inactivated HIV-1 from which gp 120 is depleted. It is found to be safe with immunogenic potential in persons infected with HIV. In initial studies it was found to improve CD4+-cell count in asymptomatic HIV cohort not taking antiretroviral agents. It is given intramuscularly as an injection into the triceps muscles. The recent study by Sukeepaisarncharoen w et at suggests that remune therapy is associated with stabilization of CD 4-cell counts. It is also suggests that it may be of value in participants with higher CD4+ T cell count.

One such immunomodulator consists of mixture of antigens of inactivated bacteria with antigens of influenza virus (poly antigenic immunomodulator). It has not been possible to achieve improvement in CD4+ count using it.

SB-73 is another immunomodulator made up of substance produced by pencillium P (PB-73 strain). In a small study it is found to improve CD4+ count in majority (10/14) of individuals, infected with HIV when given intramuscularly in a dose of 5 mgm.

Reticulose, a peptide-nucleic acid is another immunomodulator found to be useful in improving CD4+ count in HIV infected individuals when given subcutaneously.

It was given as two 1 ml subcutaneous (SC) injections per day for two weeks followed by 1 ml SC per day every other week for a total 60 days (30 days total treatment). It resulted in a significant improvement, in CD4+ count in absence of any other antiretroviral therapy.

Thymosin $\alpha_1$ is a 28-aminoacid peptide. It was evaluated for its efficacy to improve CD4+ along with interleukin-2. It was found to have no significant effect. Grenulocyte colong stimulating factor (Filgrastim) has also been evaluated to improve immune response in HIV without much success.

OKT3, a CD3 monoclonal antibody, has been successfully used in management of HIV along with antiretroviral and Interleukin-2 in three patients.

Of various cytokines used in management of HIV, Interleukin-2 (IL-2) is extensively studied and used. It is used as injection to be administered intravenously or subcutaneously. It is found to improve CD4+ count significantly when used alone or along with antiretroviral drugs. It is given as intermittent therapy the side effects seen are sometimes intolerable. They are seen only during period of active administration. The improvement seen in CD4+ count is found to be stable.

Other cytokines used in management of HIV includes IL-12 and IL-15.

U.S. Pat. No. 5,759,992 provides low molecular weight glycopeptide with a molecular weight of 919.2 dalton which is derived from supernatant of disrupted cells maintaining temperature of 4° C. through out the process. This is obtained from bacteria which includes *E coli* and *Mycobacterium*. It is found to improve CD4+ count in normal mice. It is not evaluated in HIV +ve animals.

U.S. Pat. No. 5,871,732 describes methods for preventing or treating AIDS, AIDS related complex and human immunodeficiency virus infection by anti-CD4+ antibody homologs to DNA sequences of encoding such homologs.

*Mycobacterium w* is a non-pathogenic, cultivable, atypical mycobacterium, with biochemical properties and fast growth characteristics resembling those belonging to Runyons group IV class of *Mycobacteria* in its metabolic and growth properties but is not identical to those strains currently listed in this group. It is therefore thought that (Mw) is an entirely new strain. The species identity of Mw has been defined by polymerase chain reaction DNA sequence determination.

It has been found to share antigens with *Mycobacterium leprae* and *Mycobacterium tuberculosis*. It is found to provide prophylaxis against leprosy in humans by converting lepromin negative individuals to lepromin positivity. It is also found to provide prophylaxis against tuberculosis in animals. In leprosy it is also found to reduce duration of therapy for bacterial killing, clearance as well as clinical cure when used along with multi drug therapy.

REFERENCES

1. Immunological parameters modified in HIV disease by the macrophage activity immunomodulator WF 10 (a phase II pathogenesis study) Hemdier B; Lull R Ah Ching O; Broz M; Kuehne F W; Kahn J IntConfAIDS. 1998; 12: 347-8
2. Changes in viral expression and cytokine profile induced by a polyantigenic immunomodulator in HIV-infected peripheral blood mononuclear cells. Rios Z; Rios E O; Garcia M I; De Leon C; Guzman L M; Rodriguez W; Romero D Hunter R. Cell Mol Biol (Noisy-le-grand). 1995; 41 Suppl 1: s93-101.
3. Controlled clinical trial of reticulose, a peptide-nucleic acid with Immunomodulator activity, in patients with HIV infection. Levett P N; Roach T C; Hirschman S Z; Broome H; Fraser H S Abstr Gen Meet Am Soc Microbiol. 1998 May 17-21; 98: 53
4. Survival and quality of life in HIV-positive patients treated with poly antigenic immunomodulator.
Colon J I; Encamacion G; Ortiz Santini M R; Rodriguez Malave M T; Santiago Delpin E A; Marchand A M P R Health Sci J. 1997 March; 16 (1): 9-14.
5. SB-73 immunomodulator: phase II clinical trial on HIV infection. Bellucci S; Abreu W; Bertazzoli R; Tomita F; Lourenco C; Machodo L; Silva O Int Conf AIDS. 1992 July 19-24; 8 (3): 54
3. Interleukin-15 Triggers Activation and Growth of the CD8 T-Cell Pool in Extravaxcular Tissues of Patients With Acquired Immunodificiency Syndrome.
Agostini C, Trentin L, Sancetta R, Facco M, Tassinari C, Cerutti A, Bortolin M, Milani A, Siviero M, Zambello R, Semenzato G.
Blood, Vol 90, No 3 (August 1), 1997: pp 1115-1123
4. Ethylene Glycol-Modified Interleukin-2 and Thymosin a) in Human immunodeficiency Virus Type 1 Infection; Journal of Infectious Disease, 1996; 173; 1005-8 I
5. OKT3 and IL-2 treatment for purging of the latent HIV-1 reservoir in vivo results in selective long-lasting CD4+ T cell depletion. van Praag R M, Prins J M, Roos M T, Schellekens P T, Ten Berge I J, Yong S L, Schuitemaker H, Eerenberg A J, Jurriaans S, de Wolf F, Fox C H, Goudsmit J. Miedema F, Lange J M J Clin Immunol 2001 May; 21 (3): 218-26
6. How effective are complementary therapies for HIV and AIDs ?—A systemic review. Ozsoy M, Ernst E.
Int J STD AIDS 1999 October; 10 (10): 629-35
7. Mechanism of HIV persistence: implications for vaccines and therapy.
Bremermann H J J Acquir Immune Defic Syndr Hum Retrovirol 1995 Aug. 15; 9 (5): 459-83.
8. Both serum HIV type 1 RNA levels and CD4+ lymphocyte counts predict clinical outcome in HIV type 1-infected subjects with 200 to 500 CD4+ cells per cubic millimeter. AIDs clinical trials group study 175 virology study team.
Kim S, Hughes M D, Hammer S M, Jackson J B, DeGruttola V, Katzenstein D A.
AIDs Res Hum Retroviruses 2000 May 1; 16 (7): 645-53.
9. Do HIV type 1 RNA levels provide additional prognostic value to CD4+ lymphocyte counts in patients with advanced HIV type 1 infection? AIDs Res Hum Retroviruses 2001 Aug. 10; 17 (12): 1099-105.
10. Guidelines for the Use of Antiretroviral Agents in HIV-Infected Adults and Adolescents. Aug. 13, 2001 (This guidelines were developed by the Panel on Clinical Practices for Treatment of HIV Infection convened by the Department of Health and Human Services (DHHS) and the Henry J. Kaiser Family Foundation.
Leadership of the Panel consists of Anthony S. Fauci, National Institutes of Health, Bethesda, M D (co-chair); Eric P. Goosby, DHHS, Washington, D.C., (co-convener); and Jennifer Kates, Henry J. Kaiser Foundation, San Francisco, Calif., (co-convener).
11. A controlled Trial of two nucleoside analogues plus indinavir in persons with human immunodeficiency virus infection and CD4+ cell counts of 200 per cubic millimeter or less.
Arduino J M, Fischi M A, Stanley K, Collier A C, Spiegelman D.
The New Eng. Journal of Med. 1997 Sep. 337 (11): 725-733.
12. Treatment with Indinavir, Zidovudine, and Lamivudine in adults with human immunodeficiency virus infection and prior antiretroviral therapy. scott m. hammer, m. d., kathleen e. squires, m. d., michael d. hughes, ph. d., janet m. grimes, m. s. lisa m. emeter, m. d., judith s. currier, m. d., joseph j. eron, jr., m. d., judith e. feinberg, m. d., henry h. balfour, jr., m. d., lawrence. eyton, m. d., jeffrey a. chodakewitz, m. d., et al.
The New Eng. Journal of Med. 1997 September 337 (11): 734-739.
13. Ramdomised placebo-controlled trial of ritonavir in advanced HIV-1 disease Yazdanpanah Y, Chene G, Losina E, Goldie S J, Merchadou L D, Alfandari S, Seage G R 3rd, Sullivan L, Marimoutou C, Paltiel A D, Salamon R, Mouton Y, Freedberg K A.
Int J. Epidemiol. 2001 August; 30 (4): 864-71.
22. Randomise trial of intradennal *Mycobacterium vaccae* or intradermal hepatitis 13 immunisation in children with HIV infection.
Johnson D, Waddell R D, Pelton S I, Jaeger A S, Mod) in J F, Yogev R, Morin P, Arbeit R D, von Reyn C F.
Vaccine. 1999 Jun. 4; 17 (20-21): 2583-7.
23. Immunization of HIV-infected adults with a three-dose series of inactivated *Mycobacterium vaccae*.
Marsh B J, Fordham von Reyn C, Arbeit R D, Morin P.
Am J Med. Sci. 1997 June; 313 (6): 377-83.
24. Safety and immunogenicity of a five-dose series of inactivated *Mycobacterium vaccae* vaccination for the prevention of HIV-associated tuberculosis.
Waddell R D, Chintu C, Lein A D, Zumla A, Karagas M R, Baboo K S, Habbema J D, Tosteson A N, Morin P, Tvaroha S, Arbeit R D, Mwinga A, von Reyn C F.
Clin Infect Dis. 2000 June; 30 Suppl 3: S309-15.

BRIEF SUMMARY OF THE INVENTION

According to present invention, immunomodulator made from '*Mycobacterium w*' (Mw) is found to be useful in the management of HIV infection. We have now found that the same therapeutic agent not only delays development of AIDS in patients infected by HIV, but also is capable of causing regression, or even removal, of overt symptoms of AIDS even in patients where the disease is far advanced. These effects have been found in patients suffering also from tuberculosis. These effects are also seen in patients who are suffering from HIV infection with or without AIDS and without associated tuberculosis. The immunomodulator as per present invention is also found useful in relieving symptoms of HIV.

Therapeutic agent which may be used in the present invention resembles Mw a non-pathogenic, cultivable, atypical mycobacterium, with biochemical properties and fast growth characteristics resembling those belonging to Runyons group IV class of *Mycobacteria* in its metabolic and growth properties but is not identical to those strains currently listed in this group. It is therefore thought that (Mw) is an entirely new strain.

The species identity of Mw has been defined by polymerase chain reaction DNA sequence determination and differentiated from thirty other species of mycobacteria. It however differs from those presently listed in this group in on respect or the other. By base sequence analysis of a polymorphic region of pattern analysis, it has been established that Mw is a unique species distinct from many other known mycobacterial species examined which are: *M. avium, M. intracellulare, M. scrofulaceum, M. kansasii, M. gastri, M. gordonae, M. shimoidei, M. malmoense, M. haemophilum, M. terrae, M. nonchromogenicum, M. triviale, M. marinum, M. flavescens, M. simian, M. szulgai, M. xenopi, M. asciaticum, M. aurum, M. smegmatis, M. vaccae, M. fortuitum* subsp *fortuitum, M. fortuitum* subsp. *Peregrinum, M. chelonae* subsp. *Chelonae, M. chelonae* subsp. *Abscessus, M. genavense, M. tuberculosis, M. tuberculosis* H37RV *M. paratuberculosis*.

The object of the present invention is to provide an immunomodulator *Mycobacterium w* containing '*Mycobacterium w*' (Mw) with or without obtained from Mw for the prophylaxis or therapy of AIDS or AIDS related complex, to a subject exposed to HIV infection or is HIV positive with or without overt symptoms of AIDS.

Yet another object of the invention is to provide immunomodulator derived from *Mycobacterium w* that are useful for the management of HIV infection.

Yet another object of the invention is to provide immunomodulator derived from *Mycobacterium w* to improve immune function of HIV +ve subjects.

Yet another object of present invention is to provide immunomodulator to improve CD4+ count in HIV infected individuals.

Yet another object of present invention is to provide immunomodulator effective in ameliorating symptoms associated with HIV infection.

Yet another object of present invention is to provide an immunomodulator effective in management of opportunistic infections of associated with HIV infection.

Yet another object to present invention is to provide an immunomodulator useful in improving immune function of HIV +ve subjects in presence or absence of antiretroviral drugs.

Yet another object of the invention is to provide methods for the treatment of HIV, which results in the amelioration of symptoms of symptomatic stage of the disease.

It is yet another object of the invention to provide for a method of treatment of HIV infection that results in improved CD4+ T cell count.

DETAILED DESCRIPTION OF THE INVENTION

Figure 1:
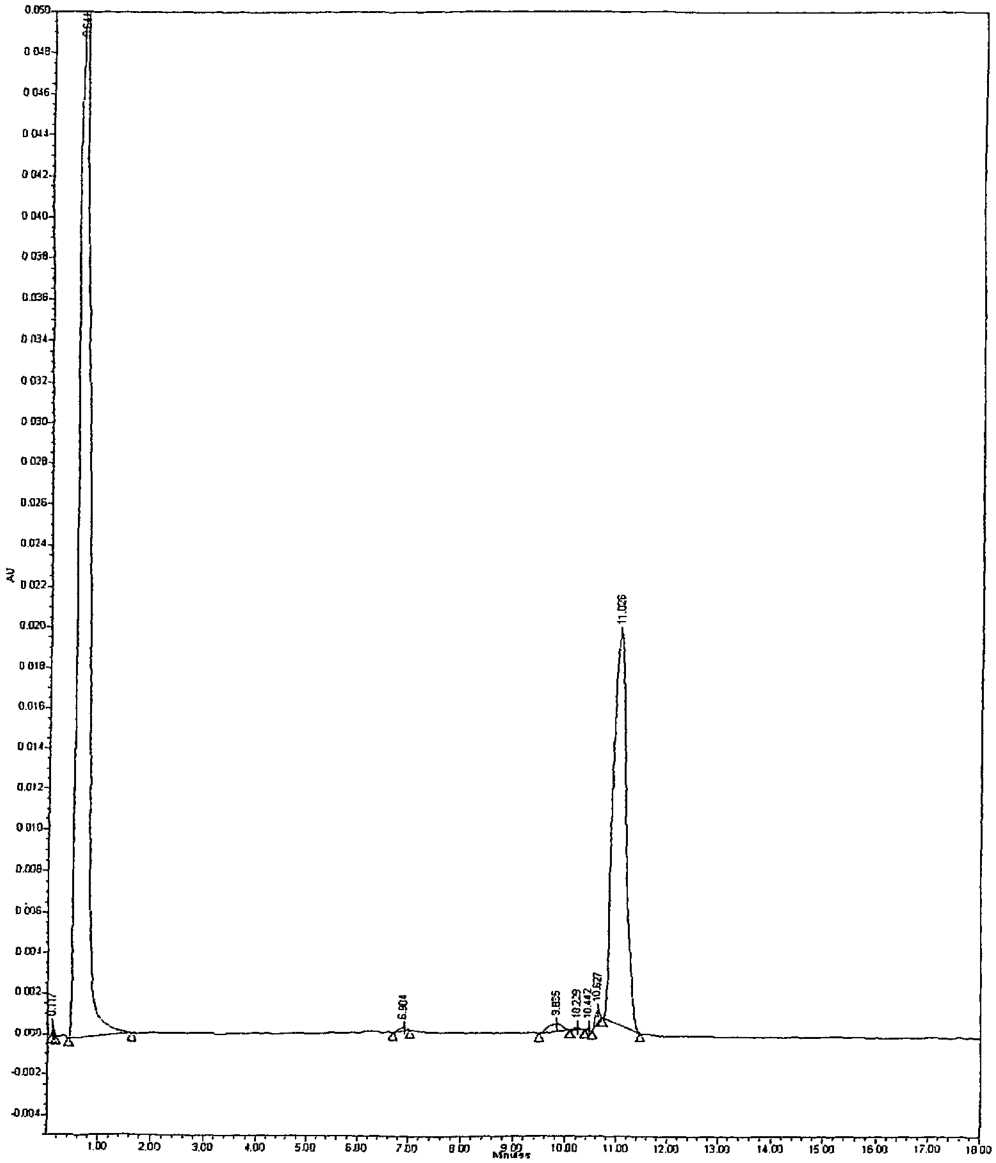
FIG. 1. HPLC analysis of crude extract obtained after disruption of *Mycobacterium w* cell by sonication.
Figure 2:
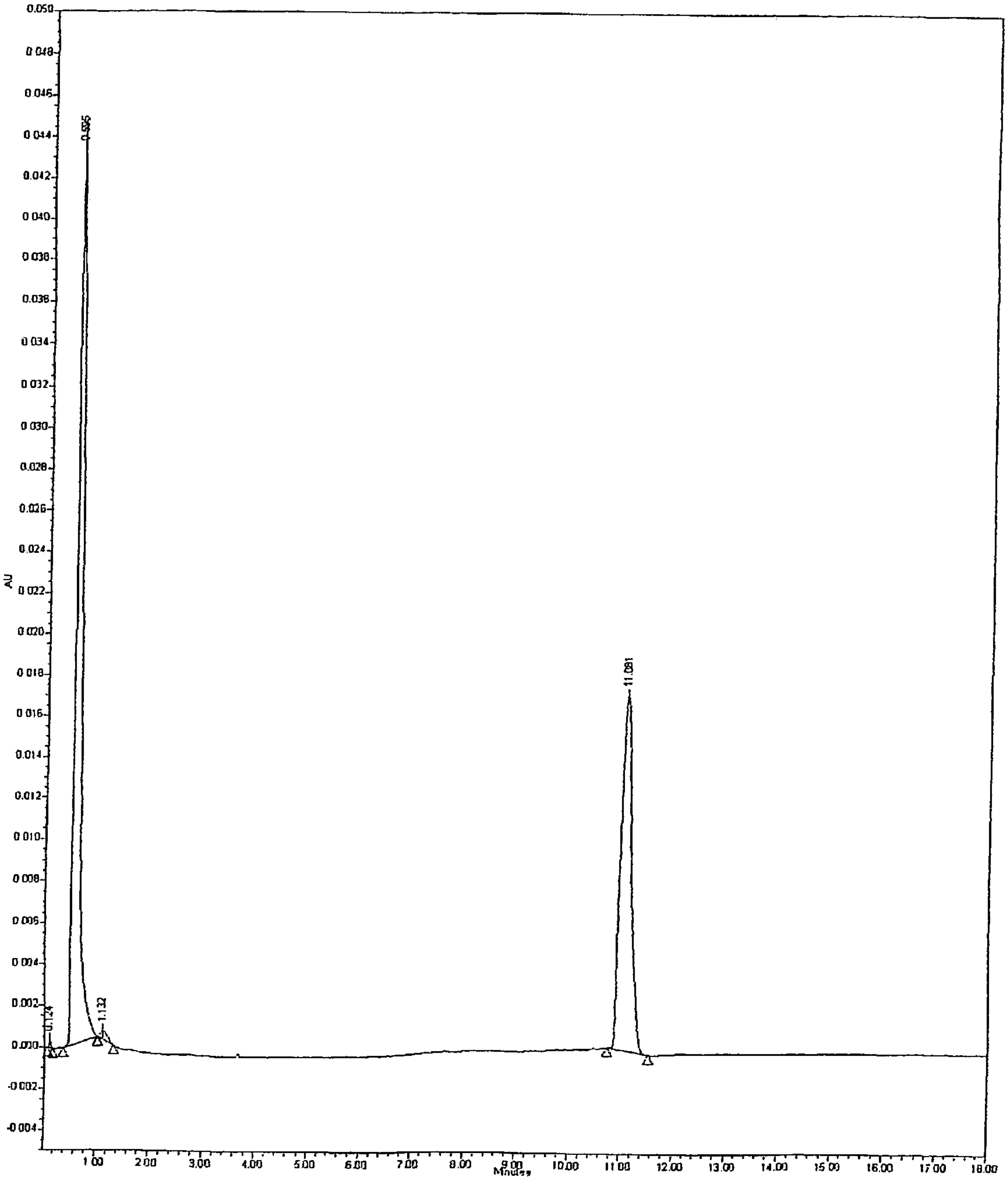
FIG. 2 HPLC analysis of methanol extract of *Mycobacterium w*.
Figure 3:
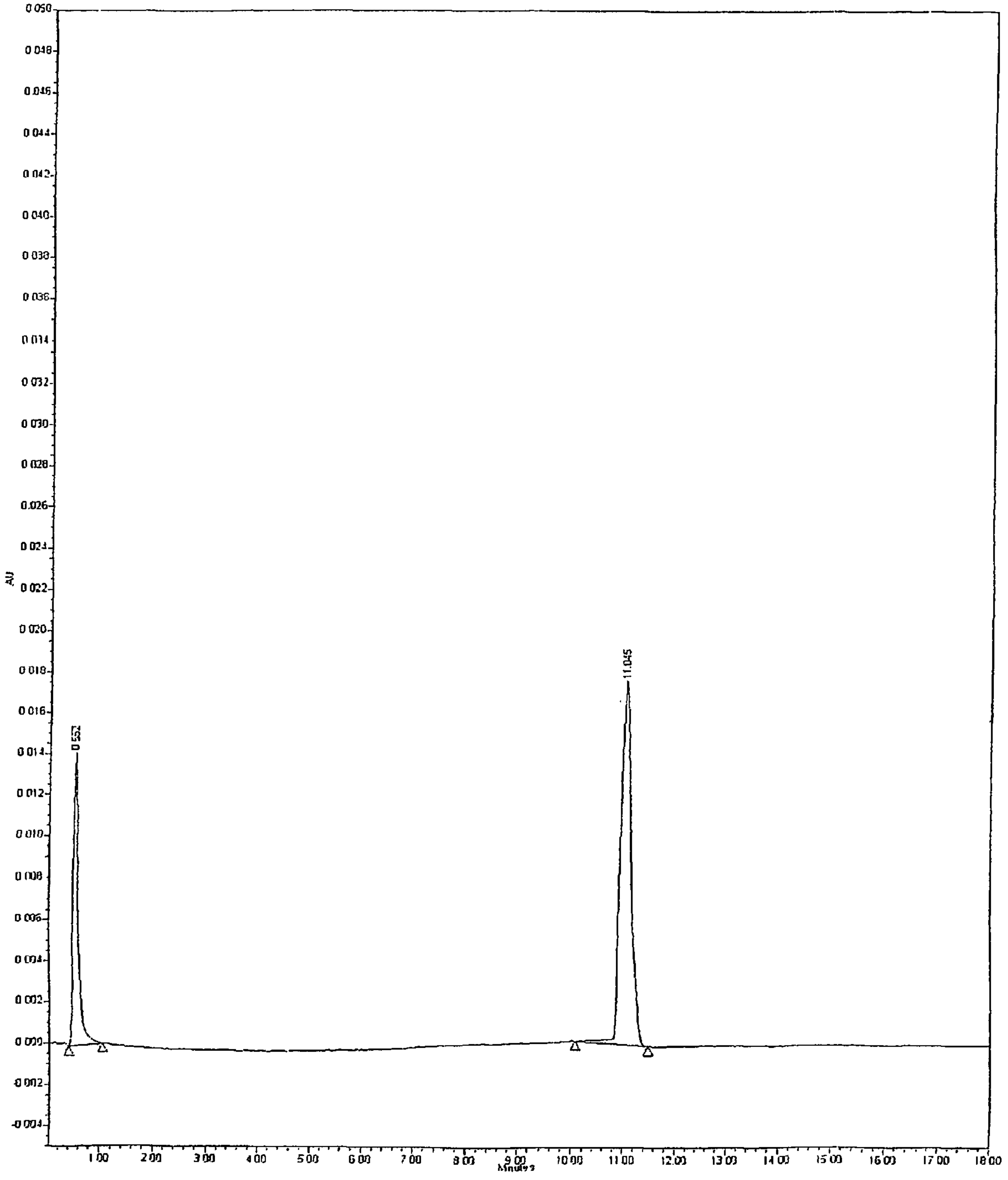
FIG. 3 HPLC analysis of chloroform extract of *Mycobacterium w*.
Figure 4:
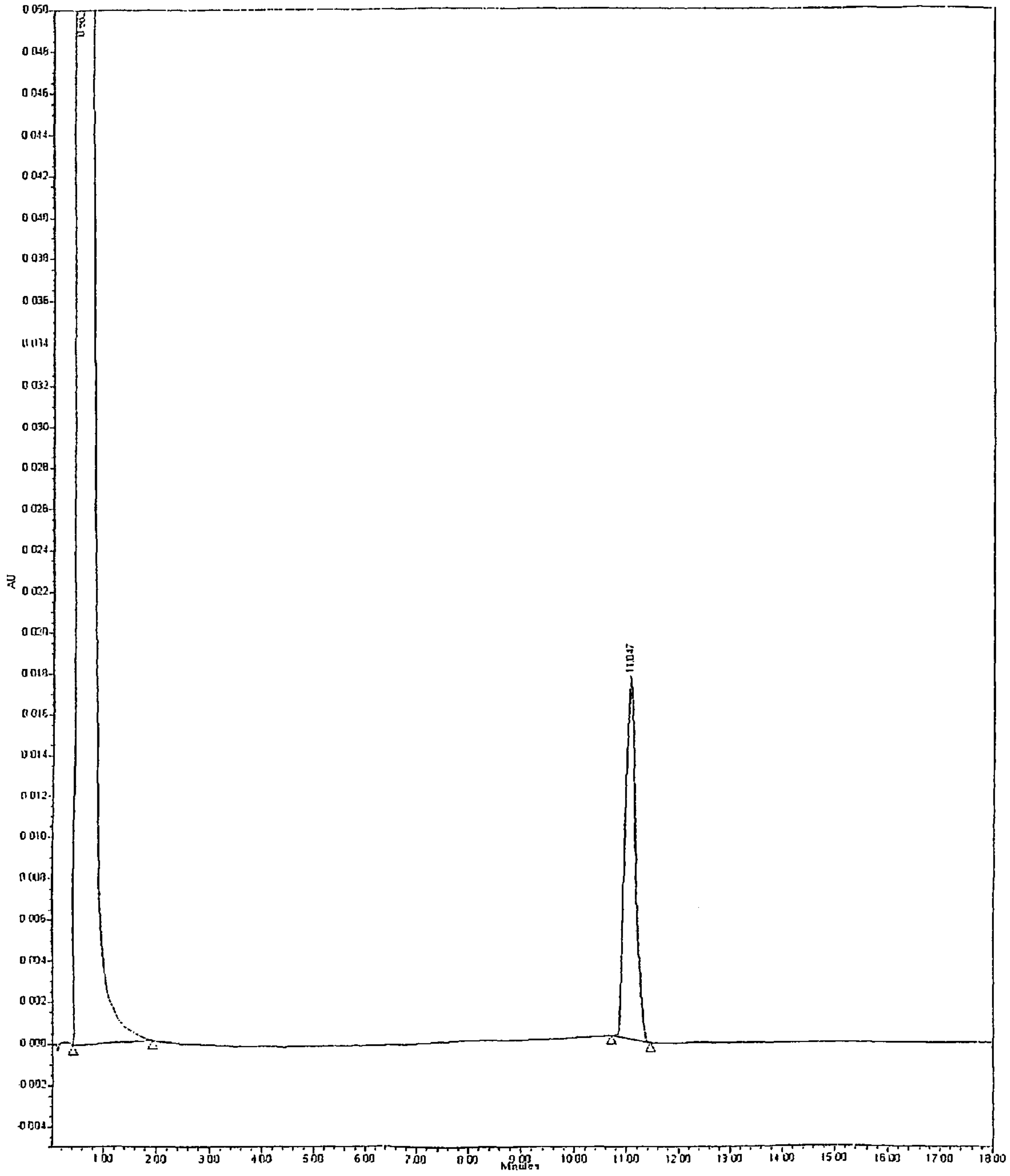
FIG. 4 HPLC analysis of acetone extract of *Mycobacterium w*.

In accordance with the invention the composition of immunomodulator the method of preparation, HPLC characteristic its safety and tolerability, methods of use and outcome of treatments are described in following examples. The following are illustrative examples of the present invention and scope of the present invention should not be limited by them.

EXAMPLE 1

The Immunomodulator Compositions

| A. Each dose of 0.1 ml of therapeutic agent contains: | |
|---|---|
| *Mycobacterium w*., (heat killed) | $0.50 \times 10^9$ |
| Sodium Chloride I.P. | 0.90% w/v |
| Thiomerosal I.P. (As a Preservative) | 0.01% w/v |
| Water for injection I.P. | q.s. to 0.1 ml |
| B. Each dose of 0.1 ml of therapeutic agent contains Extract of *Mycobacterium w* after sonication from $1 \times 10^{10}$ *Mycobacterium w* | |
| Sodium Chloride I.P. | 0.90% w/v |
| Thiomerosal I.P. (As a Preservative) | 0.01% w/v |
| Water for injection I.P. | q.s. to 0.1 ml |
| C. Each dose of 0.1 ml of therapeutic agent contains Methanol Extract of $1 \times 10^{10}$ *Mycobacterium w* | |
| Sodium Chloride I.P. | 0.90% w/v |
| Thiomerosal I.P. (As a Preservative) | 0.01% w/v |
| Water for injection I.P. | q.s. to 0.1 ml |
| D. Each dose of 0.1 ml of therapeutic agent contains Chloroform Extract of $1 \times 10^{10}$ *Mycobacterium w* | |
| Sodium Chloride I.P. | 0.90% w/v |
| Thiomerosal I.P. (As a Preservative) | 0.01% w/v |
| Water for injection I.P. | q.s. to 0.1 ml |
| E. Each dose of 0.1 ml of therapeutic agent contains Acetone Extract of $1 \times 10^{10}$ *Mycobacterium w* | |
| Sodium Chloride I.P. | 0.90% w/v |
| Thiomerosal I.P. (As a Preservative) | 0.01% w/v |
| Water for injection I.P. | q.s. to 0.1 ml |
| F. Each dose of 0.1 ml of therapeutic agent contains Ethanol Extract of $1 \times 10^{10}$ *Mycobacterium w* | |
| Sodium Chloride I.P. | 0.90% w/v |
| Thiomerosal I.P. (As a Preservative) | 0.01% w/v |
| Water for injection I.P. | q.s. to 0.1 ml |

-continued

| G. Each dose of 0.1 ml of therapeutic agent contains Liticase Extract of $1 \times 10^{10}$ *Mycobacterium w* | |
|---|---|
| Sodium Chloride I.P. | 0.90% w/v |
| Thiomerosal I.P. (As a Preservative) | 0.01% w/v |
| Water for injection I.P. | q.s. to 0.1 ml |
| H. Each dose of 0.1 ml of therapeutic agent contains *Mycobacterium w* (heat killed) $0.5 \times 10^7$ Extract of *mycobacterium w* obtained *Mycobacterium w* by disruption, solvent extraction or enzymatic extraction. | |
| Sodium Chloride I.P. | 0.90% w/v |
| Thiomerosal I.P. (As a Preservative) | 0.01% w/v |
| Water for injection I.P. | q.s. to 0.1 ml |

EXAMPLE 2

The Process of Preparing Immunomodulator

A. Culturing using of *Mycobacterium w.* i) Preparation of Culture Medium.

*Mycobacterium w* is cultured on solid medium like L J medium or liquid medium like middle brook medium or sauton's liquid medium.

For better yield middle brook medium is enriched. It can be preferably enriched by addition of glucose, bactotryptone, and BSA. They are used in ratio of 20:30:2 preferably.

The enrichment medium is added to middle brook medium. It is done preferably in ratio of 15:1 to 25:1 more preferably in ratio of 20:1.

ii) Bioreactor operation a) Preparation of vessel: The inner contact parts of the vessel (Joints, mechanical seals, o-ring/gasket grooves, etc.) should be properly cleaned to avoid any contamination. Fill up the vessel with 0.1 N NaOH and leave as such for 24 H to remove pyrogenic materials and other contaminants.

The vessel is then cleaned first with acidified water, then with ordinary water. Finally, the vessel is rinsed with distilled water (3 times) before preparing medium.

b) Sterilization of bioreactor The bioreactor containing 9 L distilled water is sterilized with live steam (indirect). Similarly the bioreactor is sterilized once more with Middlebrook medium. The other addition bottles, inlet/outlet air filters etc. are autoclaved (twice) at 121° C. for 15 minutes. Before use, these are dried at 50° C. oven.

c) Environmental parameter i. Temperature: 37±0.5° C.

ii. pH: 6.7 to 6.8 initially.

B. Harvesting and concentrating

It is typically done at the end of $6^{th}$ day after culturing under aseptic condition.

The concentration of cells (palletisation) is done by centrifugation.

C. Washing of cells

The pallet so obtained is washed minimum three times with normal saline. It can be washed with any other fluid which is preferably isotonic.

D. Adding pharmaceutically acceptable carrier.

Pyrogen free normal saline is added to pallet. Any other pyrogen free isotonic fluid can be used as a pharmaceutical carrier. The carrier is added in amount so as get to desired concentration of active in final form.

E. Adding preservative to keep the product free from other contaminating bacteria for its self life preservative is added. Preferred preservative is thiomesol which is used in final concentration of 0.01% w/v.

F. Terminal Sterilization Terminal sterilization can done by various physical methods like application of heat or ionizing radiation or sterile filtration.

Heat can be in the form of dry heat or moist heat. It can also be in the form of boiling or pasteurization.

Ionizing radiation can be ultraviolet or gamma rays or microwave or any other form of ionizing radiation.

It is preferable to autoclave the final product.

This can be done before after filling in a final packaging.

G. Quality Control i. The material is evaluated for purity, sterility.

ii. The organisms are checked for acid fastness after gram staining.

iii. Inactivation test: This is done by culturing the product on L J medium to find out any living organism.

iv. Pathogenicity and/or contamination with pathogen.

The cultured organisms are infected to Balb/c mice.

None of the mice should die and all should remain healthy and gain weight. There should not be any macroscopic or microscopic lesions seen in liver, lung spleen or any other organs when animals are killed upto 8 weeks following treatment.

v. Biochemical Test:

The organism is subjected to following biochemical tests:

a) Urease b) Tween 80 hydrolysis c) Niacin test d) Nitrate reduction test

The organism gives negative results in urease, tween 80 hydrolysis and niacin test. It is positive by nitrate reduction test.

H. Preparation of constituents of *Mycobacterium w.*

The constituents of *Mycobacterium w* can be prepared for the purpose of invention by:

I. Cell disruption

II. Solvent extraction

III. Enzymatic extraction.

The cell disruption can be done by way of sonication or use of high pressure fractionometer or by application of osmotic pressure ingredient.

The solvent extraction can be done by any organic solvent like chloroform. ethanol, methanol, acetone, phenol, isopropyl alcohol, acetic acid, urea, hexane etc.

The enzymatic extraction can be done by enzymes which can digest cell wall/membranes. They are typically proteolytic in nature. Enzyme liticase and pronase are the preferred enzymes. For the purpose of invention cell constituents of *Mycobacterium w* can be used alone in place o I *Mycobacterium w* organisms or it can be added to the product containing *Mycobacterium w.*

Addition cell constituents results in improved efficacy of the product.

EXAMPLE 3

Characteristics of Constituents of *Mycobacterium w* by HPLC Analysis

The constituents of *Mycobacterium w.* used for the purpose of invention when subjected to HPLC analysis gives a single peak at 11 minutes. No other significant peaks are found beyond. The peak is homogenous and devoid of any notch suggesting homogeneity of material obtained HPLC analysis was done using a waters system high performance liquid chromatography apparatus Column: Novapak c1860A, 4 μm, 3. 9×150 mm.

The guard column: Novapak c 18

Column Temperature: 30° C.

Flow rate: 2.5 ml/min

Injection volume: 25 μL.

Mobile phase:

Solvent A: HPLC grade methanol.

Solvent B: HPLC grade methylene chloride

Binary gradient:

The HPLC gradient initially comprised 98% (v/v) methanol (solvent B).

The gradient was increased linearly to 80%.

A and 20% B at one minute; 35% A and 65% B at 10 minutes, held for 5 seconds and then decreased over 10 seconds back to 98% A and 2% B.

EXAMPLE 4

Safety of Immunomodulator

*Mycobacterium w* when used in healthy animals or humans is found to be safe well tolerated and has no effect on any organ system, biochemistry or hematology including various blood cells. It is found not to cause lymphocytosis and nor change ratio of CD4+:CD8 cells as seen with various other nonspecific immune stimulation.

The only effect seen is at injection site. It includes morphologically formation of erythema, induration ulceration and scar formation. Histologically the injection site is found to have infiltration of various kinds of lymptocytes, plasma cells, giant cells giving a histological picture of epitheloid cell granulomas.

EXAMPLE 5

Effect of Immunomodulator on Symptomatic HIV +ve Patients 11 subjects who were HIV +ve and getting recurrent attacks of fever, upper respiratory tract infection, and diarrhea were given *Mycobacterium w* ($5\times10^8$) intradermally. All improved and showed no recurrence of symptoms after $2^{nd}$ month of treatment.

EXAMPLE 6

Effect of Immunomodulator on CD4+Count in HIV 1 Infected Adult Patients a) When Immunomodulator alone is used:

In 17 HIV positive individuals who had symptoms attributed to HIV and seeking help for the same *Mycobacterium w* was used as a sole therapy. *Mycobacterium w* was administered intradermally over a deltoid region. The amount of *Mycobacterium w* injected was $5\times10^8$ in a single injection. At the time of inclusion in study *Mycobacterium w* was given as intradermal injection over both the deltoids making a total dose of $1\times10^9$ *Mycobacterium w* subsequently at the interval of a month a single intradermal injection was given over a deltoid region which included $5\times10^8$ organisms.

There was no mortality or morbidity seen during trial. All subjects tolerated the therapy well and completed the trial. Symptomatic relief was seen within two months of initiation of therapy.

All subjects were evaluated for their CD4+ count at the beginning of therapy and 5 months later. The mean pretreatment CD4+ count was 204.70 (range 430-6).

All subjects showed improvement in CD4+ count. At the end of 5 months mean change in CD4+ count was 163.17 (range 8-628). In seven (41.2%) individuals increase in CD4+ count was more than 80%. Improvement in CD4+ count was less than 40% in 3 individuals (17.6%) only.

The therapy was not associated with any side effects systemically. These were a local reaction seen at the site of injection. It was in the form of erythematous reaction which was associated with induration. It progressed to ulceration at the site of injection in few which healed spontaneously leaving behind a this scar.

None of the subjects participating in a trial received any antiretroviral therapy.

Summary of Results

| | | |
|---|---|---|
| A | No. of HIV +ve subjects | 17 |
| B | Mean base line CD4+ count | 204.70 |
| C | Mean post treatment CD4+ count | 368.93 |
| | Range | 850 to 32 |
| D | Change in CD4+ count | 163.17 (104.43%) |
| | Range | 628 to 8 (433.33 to 4.08%) |

Details of change in CD4+ count in each individuals. (Table 1)

TABLE 1

| NO. | PRETREATMENT CD4+ COUNT | POST-TREATMENT CD4+ | CHANGE (NO.) | CHANGE (%) |
|---|---|---|---|---|
| 1 | 168 | 270 | 102 | 60.7 |
| 2 | 302 | 948 | 628 | 196 |
| 3 | 298 | 453 | 155 | 52 |
| 4 | 280 | 496 | 216 | 77 |
| 5 | 120 | 182 | 62 | 51.6 |
| 6 | 330 | 620 | 290 | 88 |
| 7 | 430 | 850 | 420 | 97.6 |
| 8 | 226 | 338 | 112 | 49.5 |
| 9 | 294 | 519 | 225 | 76.7 |
| 10 | 47 | 61 | 14 | 29.78 |
| 11 | 112 | 224 | 112 | 100 |
| 12 | 196 | 204 | 8 | 4.08 |
| 13 | 186 | 384 | 198 | 106.5 |
| 14 | 182 | 270 | 88 | 48.35 |
| 15 | 42 | 110 | 68 | 161.90 |
| 16 | 6 | 32 | 26 | 433.33 |
| 17 | 261 | 311 | 50 | 19.15 |
| MEAN | 204.70 | 368.93 | 163.17 | 104.43 |

The result is much better than what is achieved with use of interleukin-2 when used along with two antiretroviral drugs. It is also better than what is achieved with HAART (Highly Active AntiRetroviral Therapy) alone for the same period. It is also worth noting that all patients showed improvement of CD4+ count. Natural course of disease in absence of antiretroviral therapy is associated with decline in CD4+ count month by month. On average 12 cells are lost per month as per ziduvadine study for symptomatic individuals published in New Eng. J. Med. In a large cohort of 2664 HIV +ve asymptomatic persons the CD4+ count decline is 4.6 cells/month.

Figure 5:
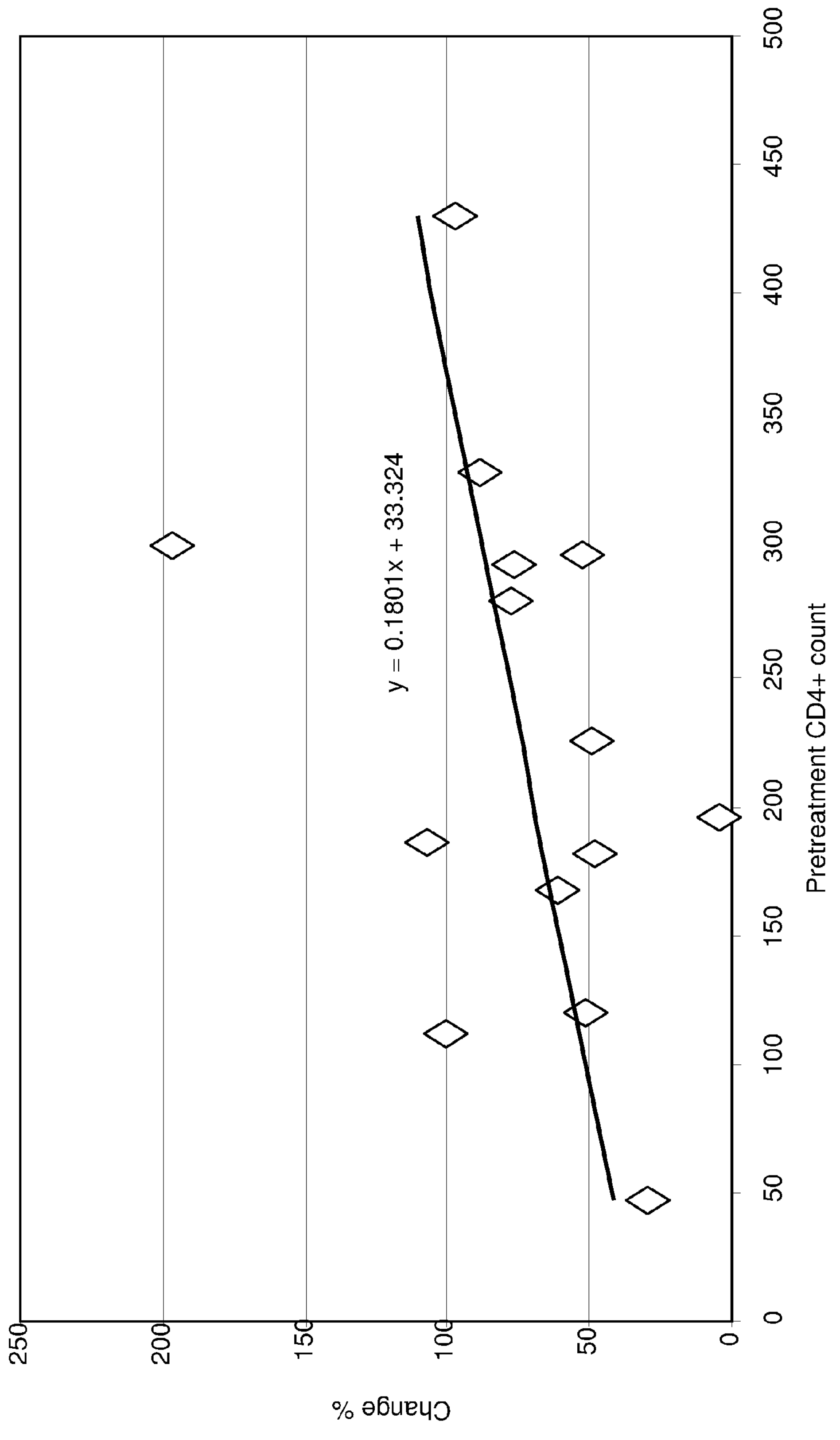
FIG. 5 Regression analysis of Pre & Post treatment change in CD4+ count when immunomodulator is used alone FIG. 6 Regression analysis of Pre & Post treatment change in CD4+ count when immunomodulator is used with two antiretroviral drugs (NRTI)

Irrespective of no. of CD4+ count at the beginning of therapy improvement in CD4+ count was seen in all individuals. The pretreatment CD4+ count ranged from 6 to 430. The regression analysis of improvement (FIG. 5) suggests that improvement seen over five month period is proportionate to initial CD4+ count. Higher the count better is improvement.

b) Two antiretroviral drugs (NRTI)+Immunomodulator

In an another set of subjects who were HIV +ve and had symptoms related to HIV *Mycobacterium w* was used along with two antiretroviral drugs (both NRTI). None of them had received any anti-retroviral prior to these. *Mycobacterium w* was administered intradermally over a deltoid region. The amount of *Mycobacterium w* injected was $5\times10^8$ in a single injection. At the time of inclusion in study *Mycobacterium w* was given as intradennal injection over both the deltoids making a total dose of $1\times10^9$ *Mycobacterium w* subsequently at the interval of a month a single intradermal injection was given over a deltoid region which included $5\times10^8$ organisms.

There was no mortality or morbidity seen during trial. All subjects tolerated the therapy well and completed the trial. Symptomatric relief was seen within two months of initiation of therapy.

All subjects were evaluated for their CD4+ count at the beginning of therapy and 5 months later. The mean pretreatment CD4+ count was 200.99 (286 TO 96). All subjects showed improvement in CD4+ count. At the end of 5 months mean change in CD4+ count was 137.37 (range 24-588)

The therapy was not associated with any side effects systemically. These were a local reaction seen at the site of injection. It was in the form of erythematous reaction which was associated with induration. It progressed to ulceration at the site of injection in few which healed spontaneously leaving behind a this scar.

None of the subjects participating in a trial received any antiretroviral therapy.

Summary of Results

| | | |
|---|---|---|
| A | No. of HIV +ve subjects | 16 |
| B | Mean base line CD4+ count | 200.99 |
| C | Mean post treatment CD4+ count | 338.37 |
| | Range | 860 to 199 |
| D | Change in CD4+ count | 137.37 (68.44%) |
| | Range | 58 to 24 (294.15 to 16%) |

Details of change in CD4+ count in each individuals. (Table 2)

TABLE 2

| NO. | PRETREATMENT CD4+ COUNT | POST-TREATMENT CD4+ | CHANGE (NO.) | CHANGE (%) |
|---|---|---|---|---|
| 1 | 162 | 238 | 76 | 47 |
| 2 | 192 | 240 | 48 | 25 |
| 3 | 286 | 860 | 574 | 200 |
| 4 | 142 | 199 | 57 | 40 |
| 5 | 250 | 290 | 40 | 16 |
| 6 | 196 | 230 | 34 | 17.3 |
| 7 | 238 | 504 | 266 | 111.76 |
| 8 | 216 | 328 | 112 | 51.85 |
| 9 | 236 | 824 | 588 | 249.15 |
| 10 | 194 | 236 | 42 | 21.64 |
| 11 | 96 | 210 | 114 | 118.75 |
| 12 | 262 | 319 | 57 | 21.75 |
| 13 | 244 | 310 | 66 | 27.04 |
| 14 | 160 | 210 | 50 | 31.25 |
| 15 | 230 | 280 | 50 | 21.73 |
| 16 | 112 | 136 | 24 | 21.42 |
| Mean | 200.99 | 338.37 | 137.37 | 68.44 |

All subjects were evaluated for their CD4+ count at the beginning of therapy and 5 months later. None of the subjects showed deterioration in CD4+ count. All irrespective of pretreatment CD4+ count (Range 96 to 286) showed improvement in CD4+ count. Natural course of disease suggest minimal or no change in CD4+ when two antiretroviral drugs are used as used in this study. Thus improvement seen in the steady is significantly much more and can not be attributed to antiretroviral therapy used in the study.

Figure 6:
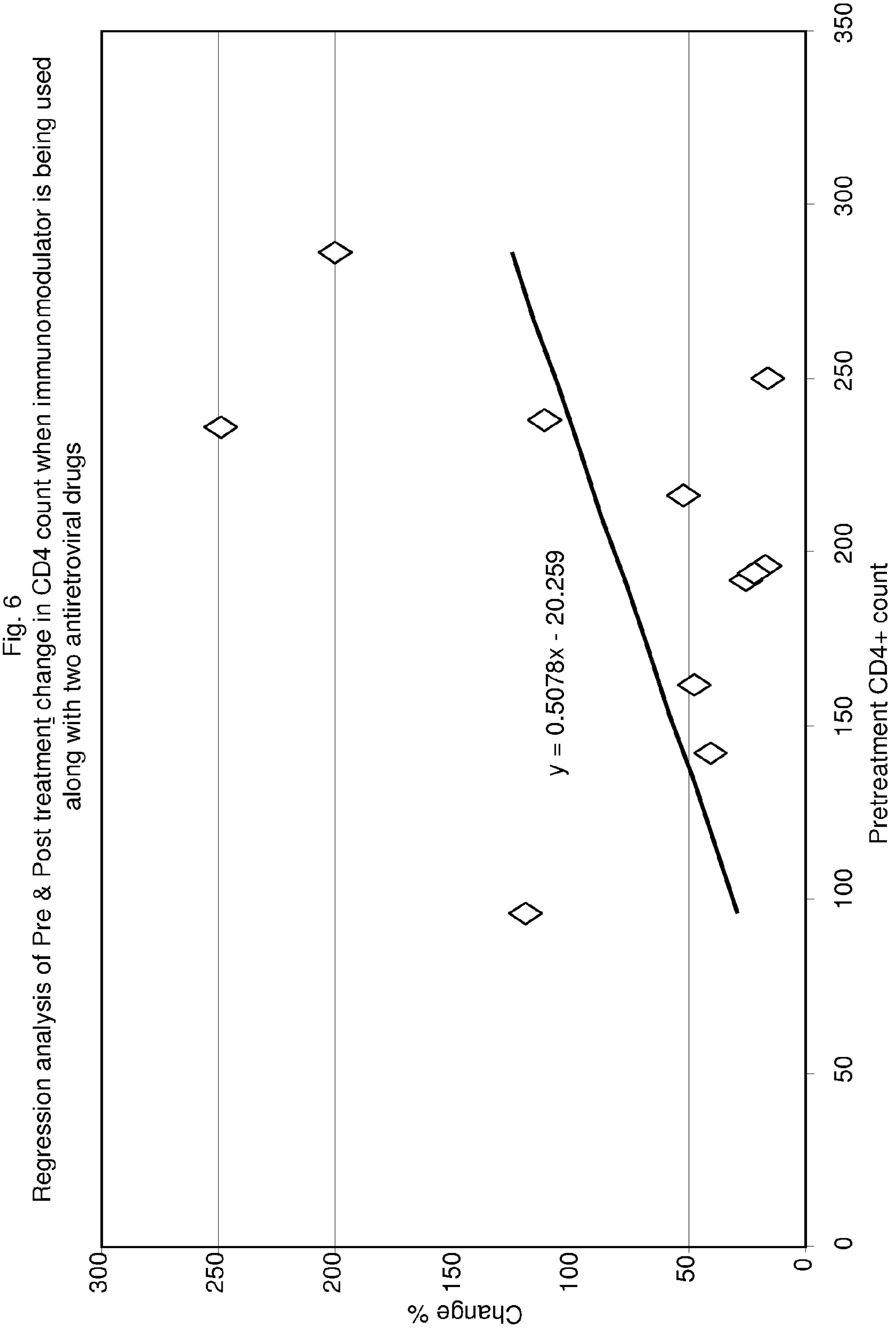

Regression analysis (FIG. 6) shows that improvement seen in CD4+ count is proportionate to the initial CD4+ count. Higher the initial count better is improvement following therapy comparison of improvement between patients receiving antiretroviral therapy (two drugs) and those not receiving therapy shows that rate of improvement is better without use of two antiretroviral drugs when initial CD4+ count is low. However when initial CD4+ count is high the rate of improvement is better when two anti-retroviral drugs are used.

c) HAART Therapy+Immunomodulator

In an another set of subjects who were HIV +ve and had symptoms related to HIV. *Mycobacterium w* was administered along with HAART therapy (three drugs). None of them had received any anti-retroviral prior to this. *Mycobacterium w* was administered intradermally over a deltoid region. The amount of *Mycobacterium w* injected was $5\times10^8$ in a single injection. At the time of inclusion in study *Mycobacterium w* was given us intradermal injection over both the deltoids making a total dose of $1\times10^9$ *Mycobacterium w* subsequently at the interval of a month a single intradermal injection was given over a deltoid region which included $5\times10^8$ organisms.

There was no mortality or morbidity seen during trial. All subjects tolerated the therapy well and completed the trial. Symptomatic relief was seen within two months of initiation of therapy.

All subjects were evaluated for their CD4+ count at the beginning of therapy and 5 months later. The mean pretreatment CD4+ count was 213.23 (range 536-40).

All subjects showed improvement in CD4+ count. At the end of 5 months mean change in CD4+ count was 258.79 (range 40-887).

The therapy was not associated with any side effects systemically. These were a local reaction seen at the site of injection. It was in the form of erythematous reaction which was associated with induration. It progressed to ulceration at the site of injection in few which healed spontaneously leaving behind a this scar.

None of the subjects participating in a trial received any antiretroviral therapy.

Summary of Results

| | | |
|---|---|---|
| A | No. of HIV +ve subjects | 17 |
| B | Mean base line CD4+ count | 213.23 |
| C | Mean post treatment CD4+ count | 445.58 |
| | Range | 1423 to 130 |
| D | Change in CD4+ count | 258.79 (155.85%) |
| | Range | 887 to 40 (338.88 to 17.4%) |

TABLE 3

| Details of change in CD4+ count in each individuals. (Table 3) | | | | |
|---|---|---|---|---|
| NO | PRETREATMENT CD4+ COUNT | POST-TREATMENT CD4+ | CHANGE (NO. | CHANGE (%) |
| 1 | 72 | 220 | 148 | 205 |
| 2 | 130 | 230 | 100 | 77 |
| 3 | 40 | 130 | 90 | 225 |
| 4 | 230 | 270 | 40 | 17.4 |
| 5 | 127 | 276 | 149 | 117 |
| 6 | 148 | 336 | 188 | 127 |
| 7 | 230 | 490 | 260 | 113.04 |
| 8 | 356 | 950 | 594 | 166.85 |
| 9 | 199 | 432 | 233 | 117.08 |
| 10 | 236 | 539 | 303 | 128.38 |
| 11 | 204 | 660 | 456 | 223.5 |
| 12 | 536 | 1423 | 887 | 165.48 |
| 13 | 108 | 269 | 161 | 149.07 |
| 14 | 92 | 198 | 106 | 115.21 |
| 15 | 203 | 582 | 379 | 186.69 |
| MEAN | 194.06 | 466.99 | 266.90 | 137.06 |
| 16 | 72 | 316 | 244 | 338.88 |
| 17 | 60 | 212 | 152 | 253.33 |
| MEAN | 66 | 264 | 198 | 296.10 |
| MEAN | 213.23 | 445.58 | 258.79 | 155.85 |

Figure 7:
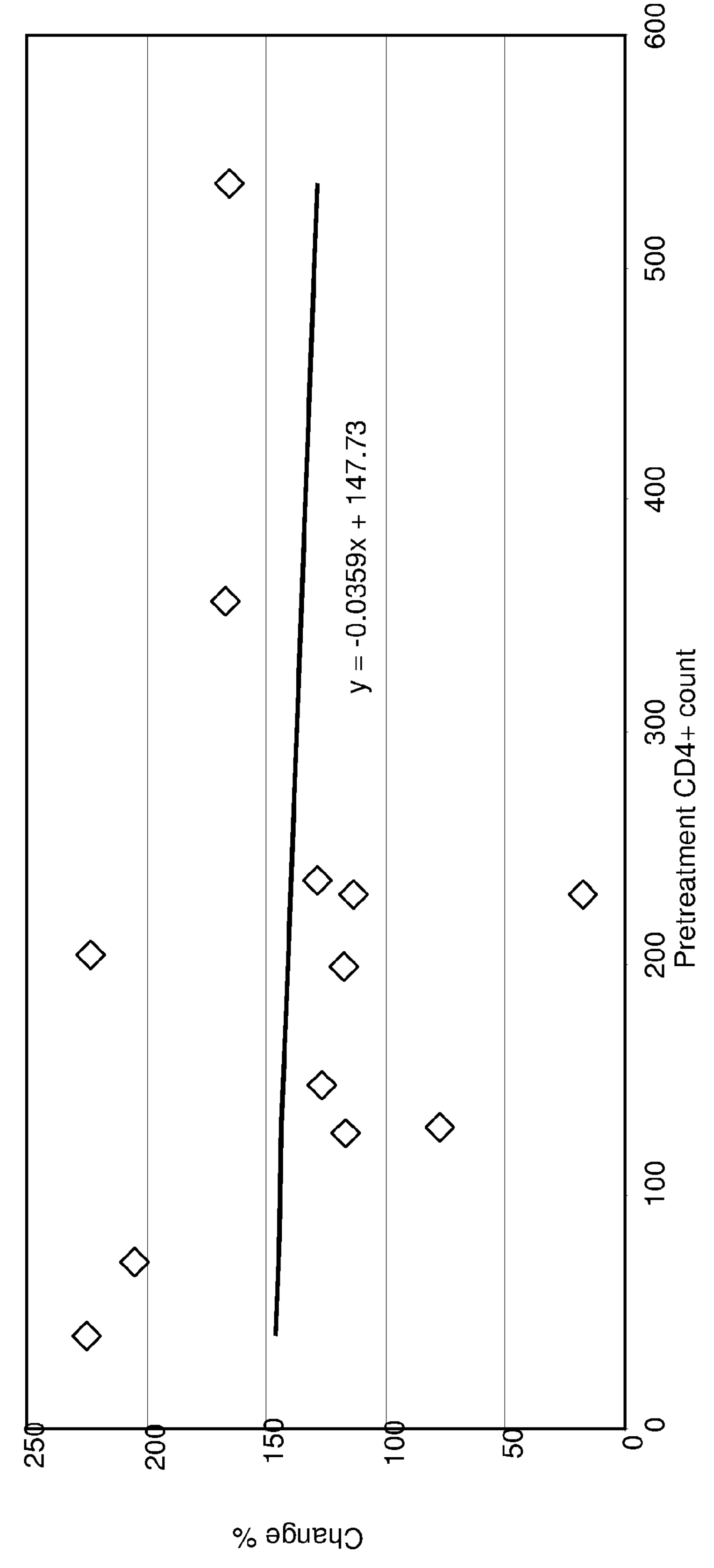
FIG. 7 Regression analysis of Pre & Post treatment change in CD4+ count when immunomodulator is used along with HAART therapy

All subjects were evaluated for change in CD4+ count at the beginning of therapy and end of therapy. All patients showed significant improvement in CD4+ count. The patients no. I to 15 had NNRTI as third drug. The patient No. 16 and 17 had protease inhibitor used as third drug. The improvement was significantly more than even reported in literature. The improvement in CD4+ count was significantly more when protease inhibitor is used compared to when NNRTI is used as part of HAART therapy. Regression analysis of results (FIG. 7) suggests that rate of improvement seen is more or less identical irrespective of initial CD4+ count. It was little lower when initial CD4+ count was higher compared to when it was lower.

EXAMPLE 7

Effect of Immunomodulator on CD4+Count in HIV-I Infected Children

Effect of Immunomodulator in children is also evaluated. Immunomodulator was given as intradermal injection of 0.1 ml every month over a deltoid region for five months. Of the five children treated with Immunomodulator alone. All showed improvement as shown in Table 4.

TABLE 4

| PRE AND POST Treatment CD4+ COUNT | | | | |
|---|---|---|---|---|
| NO. | PRETREATMENT | POST TREATEMENT | CHANGE (NO.) | CHANGE (%) |
| 28 | 506 | 1100 | 594 | 117.39 |
| 29 | 246 | 720 | 474 | 192.68 |
| 30 | 398 | 562 | 164 | 41.21 |
| 31 | 720 | 1230 | 510 | 70.83 |
| 32 | 1120 | 1460 | 340 | 30.36 |
| MEAN | 598 | 1014.4 | 416.4 | 90.49 |

Thus effect of immunomodulator is not restricted to age of HIV positive patients.

EXAMPLE 8

Effect of Immunomodulator in HIV-2 Infected Individuals

In another set of three subjects (HIV II positive), Immunomodulator alone was given as n therapy. It was given intradermally over a deltoid region. The amount of Immunomodulator injected was 0.1 ml in a single injection. At the time of inclusion in study Immunomodulator was given as intradermal injection over both the deltoids making a total dose of 0.2 ml subsequently at the interval of a month a single intradermal injection was given over a deltoid region.

All the three subjects showed improvement in CD4+ count as shown in Table 5.

TABLE 5

| No. of subjects | Gender | Pre-treatement CD4+ count | Post Treatment CD4+ count | Change in CD4+ count | % |
|---|---|---|---|---|---|
| 46 | Female | 268 | 312 | 54 | 17.30 |
| 32 | Female | 324 | 402 | 78 | 19.40 |
| 49 | Male | 363 | 427 | 64 | 14.98 |

Thus effect of immunomodulator is not found to be limited to HIV 1 only.

EXAMPLE 9

Effect of Immunomodulator in HIV +ve Subjects with Tuberculosis Cervical Lymphadenopathy not Responding to Five Anti Tuberculosis Drugs Seven HIV +ve subjects with tuberculosis cervical lymphadenopathy not responding to five anti tuberculosis drugs were given Immunomodulator intradermally. All had initial increase in size of cervical lymph node, which became erythematous. Within 3 weeks the size of lymph nodes decreased in size and over two months lymphodenopathy healed completely.

*Mycobacterium w* has been used in leprosy for faster clearance of *M. Leprae* from lesions and improved clinical out come making it possible to release the patients from therapy (MDT, multi drug therapy) at an earlier date. It has also been found to convert lepromin negative persons to lepromin positive and there by provide immunity against leprosy. According to present invention it is found useful in management of HIV. It is seen that HIV related symptoms disappear quickly when *Mycobacterium w* is administered. It is also found to improve immunity in the form of CD4+ count.

It does all this in absence of any anti retroviral therapy.

However when anti-retroviral are included along with *Mycobacterium w* in the form of HAART therapy, response is augmented.

The lack of systemic side effects as seen with all other therapies makes it even more suitable.

CD4+CD4+CD4+

We claim:

1. A method for improving CD4+ T cell mediated immunity of HIV positive patients comprising administering to said patients a therapeutically effective amount of a medicament comprising *Mycobacterium w.*

2. The method of claim 1, wherein the medicament is for managing opportunistic infections associated with HIV infection in said HIV positive patients.

3. The method of claim 1, wherein the medicament is administered for amelioration of symptoms associated with HIV.

4. A method for CD4+ T cell mediated treatment of AIDS or AIDS related complex (ARC) in HIV positive patients comprising administration of a therapeutically effective amount of a medicament comprising *Mycobacterium w.*

5. The method of claim 4, wherein the medicament is administered for delaying development of AIDS or AIDS related complex (ARC) in patients infected by HIV.

6. The method of claim 4, wherein the medicament is administered for regression or removal of symptoms of AIDS even in patients where the disease is advanced.

7. The method of claim 1 wherein the medicament improves CD4+ T cell count in said patients.

8. The method of claim 7, wherein the medicament is administered to improve a CD4+ T cell count in said patients in the absence of or in the presence of an antiretroviral therapy.

9. A method of managing or relieving symptoms associated with an HIV infection comprising administering to a patient a therapeutically effective amount of a composition comprising *Mycobacterium w.*

10. The method of claims 1 or 4, wherein the medicament further comprises adjuvants, excipients, diluents, suspending agents or preservatives.

11. The method of either of claims 1 or 4, wherein the *Mycobacterium w* is dead *Mycobacterium w.*

12. The method of claim 11, wherein the *Mycobacterium w* is killed by a physical method selected from the group consisting of heat and radiation by heat in the form of autoclaving or a combination thereof.

13. The method of claim 11, wherein the *Mycobacterium w* is killed by heat in the form of autoclaving.

14. The method of either of claims 1 or 4, wherein the medicament comprises heat killed *Mycobacterium w* obtained by sonication.

15. The method of either of claims 1 or 4, wherein the medicament is in unit dose form comprising at least $1\times10^5$ *Mycobacterium w.*

16. The method of either of claims 1 or 4, wherein the medicament is in unit close form comprising at least $1\times10^7$ *Mycobacterium w.*

17. The method of either of claims 1 or 4, wherein the medicament is in unit dose form comprising between $1\times10^8$ and $1\times10^{10}$ *Mycobacterium w.*

18. The method of either of claims 1 or 4, wherein the *Mycobacterium w* is urease negative, does not hydrolyse polyoxyethylene sorbitan monooleate, does not produce niacin or provides a strong positive response to nitrate reduction test.

19. A method of treating or ameliorating associated with human immunodeficiency virus (HIV) infection comprising administering to a patient in need thereof a composition comprising a therapeutically effective amount of *mycobacterium w.*

20. The method according to claim 9 or 19, wherein the composition further comprises Nucleoside Reverse Transcriptase Inhibitor (NRTI).

21. The method according to claim 9 or 19, wherein the composition further comprises one or more retroviral drug, wherein said drug is a component of a highly active antiretroviral therapy (HAART) therapy.

22. The method of claim 9 or 19, wherein the composition comprises in unit dose form comprising at least $1\times10^5$ *Mycobacterium w.*

23. The method of claim 9 or 19, wherein the composition comprises in unit dose form comprising at least $1\times10^7$ *Mycobacterium w.*

24. The method of claim 9 or 19, wherein the composition comprises in unit dose form comprising at least between $1\times10^8$ and $1\times10^{10}$ *Mycobacterium w.*

25. The method of claim 9 or 19, wherein the composition further comprises adjuvants, excipients, diluents, suspending agents or preservatives.

26. The method of claim 9 or 19, wherein the composition is administered by parenteral route.

27. The method of claim 9 or 19, wherein the composition is administered by intramuscular, subcutaneous or intradermal route.

28. The method of claim 8, wherein said antiretroviral therapy comprises an NRTI-based therapy or a HAART-based therapy or a combination thereof.

29. The method of claim 28, wherein the medicament further comprises adjuvants, excipients, diluents, suspending agents or preservatives.

* * * * *